(12) United States Patent
Melito et al.

(10) Patent No.: US 12,419,494 B2
(45) Date of Patent: Sep. 23, 2025

(54) MEDICAL DEVICE ACTUATOR LOCKS

(71) Applicants: Boston Scientific Scimed, Inc., Maple Grove, MN (US); Boston Scientific Medical Device Limited, Galway (IE)

(72) Inventors: Michael Melito, South Amboy, NJ (US); Aditya Dhanotiya, Madhya Pradesh (IN); Nabarun Bhowmick, West Bengal (IN); James Weldon, Newton, MA (US)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 0 days.

(21) Appl. No.: 18/441,200

(22) Filed: Feb. 14, 2024

(65) Prior Publication Data
US 2024/0180398 A1    Jun. 6, 2024

Related U.S. Application Data (63) Continuation of application No. 17/563,190, filed on Dec. 28, 2021, now Pat. No. 11,930,997.
(Continued)

(51) Int. Cl.
*A61B 1/00*      (2006.01)
*G05G 5/06*      (2006.01)
*A61B 1/273*     (2006.01)

(52) U.S. Cl.
CPC ........... *A61B 1/00066* (2013.01); *G05G 5/06* (2013.01); *A61B 1/2736* (2013.01); *G05G 2505/00* (2013.01)

(58) Field of Classification Search
CPC . F16D 41/185; B60T 7/105; F16H 2059/0282
(Continued)

(56) References Cited

U.S. PATENT DOCUMENTS

| | | | | |
|---|---|---|---|---|
| 152,574 A | * | 6/1874 | Snell-Baker | B60T 7/105 |
| | | | | 74/535 |
| 720,758 A | * | 2/1903 | Tuck et al. | B60T 7/105 |
| | | | | 74/535 |

(Continued)

FOREIGN PATENT DOCUMENTS

| | | |
|---|---|---|
| DE | 102008017300 A1 | 10/2009 |
| EP | 2 799 001 A | 12/2015 |

OTHER PUBLICATIONS

International Search Report and Written Opinion issued in International Application No. PCT/US2021/065279, issued Apr. 5, 2022 (12 pages).

*Primary Examiner* — Daniel D Yabut
(74) *Attorney, Agent, or Firm* — Bookoff McAndrews, PLLC (57) ABSTRACT

A handle of a medical device may comprise an actuator; a lock movable relative to the actuator and having a feature movable relative to the actuator; and a rack having plurality of teeth separated from one another by a plurality of gaps. The lock may be configured to move the feature from (a) a first configuration, in which the feature is disposed in the gap, between two of the plurality of teeth, such that the two teeth inhibit the actuator from rotating; to (b) a second configuration, in which the feature is disposed outside of the gap, such that the actuator is rotatable. In the second configuration, the teeth may be disposed between the feature and the actuator.

20 Claims, 10 Drawing Sheets

Related U.S. Application Data

(60) Provisional application No. 63/132,513, filed on Dec. 31, 2020.

(58) Field of Classification Search
USPC .......................................... 74/578, 536, 537
See application file for complete search history.

(56) References Cited

U.S. PATENT DOCUMENTS

| | | | | |
|---|---|---|---|---|
| 787,714 | A | * | 4/1905 | Austin .................... B60T 7/105 74/535 |
| 1,186,378 | A | * | 6/1916 | Christensen et al. ........................ B60R 25/086 70/195 |
| 1,521,308 | A | * | 12/1924 | Messenger .............. B60T 7/104 74/537 |
| 1,524,898 | A | * | 2/1925 | Whiter ..................... G05G 5/18 74/524 |
| 3,059,498 | A | | 10/1962 | Boyd |
| 2007/0137366 | A1 | * | 6/2007 | Esaki ................. F16H 59/0278 74/473.26 |
| 2020/0196834 | A1 | | 6/2020 | Tah |

* cited by examiner

MEDICAL DEVICE ACTUATOR LOCKS

CROSS-REFERENCE TO RELATED APPLICATIONS

This application is a continuation of U.S. application Ser. No. 17/563,190, filed on Dec. 28, 2021, which claims the benefit of priority under 35 U.S.C. § 119 from U.S. Provisional Application No. 63/132,513, filed on Dec. 31, 2020, each of which is incorporated by reference herein in its entirety.

TECHNICAL FIELD

Various aspects of this disclosure relate generally to devices and methods for actuators of medical devices, such as elevator levers for duodenoscopes.

BACKGROUND

Duodenoscopes may include a handle and a sheath insertable into a body lumen of a subject. The sheath may terminate in a distal tip portion, which may include features such as optical elements (e.g., camera, lighting), air/water outlets, and working channel openings. An elevator may be disposed at a distal tip and may be actuatable in order to change an orientation of a medical device/tool passed through the working channel. For example, the elevator may be pivotable or otherwise movable.

Elements in the handle may control the elements of the distal tip. For example, buttons, knobs, levers, etc. may control elements of the distal tip. The elevator may be controlled via a control mechanism in a handle, such as a lever, which may be attached to a control wire that attaches to the elevator. When an actuator (e.g., a lever) is actuated, the wire may move proximally and/or distally, thereby raising and/or lowering the elevator.

SUMMARY

Each of the aspects disclosed herein may include one or more of the features described in connection with any of the other disclosed aspects.

In one example, a handle of a medical device may comprise an actuator; a lock movable relative to the actuator and having a feature movable relative to the actuator; and a rack having plurality of teeth separated from one another by a plurality of gaps. The lock may be configured to move the feature from (a) a first configuration, in which the feature is disposed in the gap, between two of the plurality of teeth, such that the two teeth inhibit the actuator from rotating; to (b) a second configuration, in which the feature is disposed outside of the gap, such that the actuator is rotatable. In the second configuration, the teeth may be disposed between the feature and the actuator.

Any of the handles disclosed herein may have any of the following features. The feature may be biased into the first configuration. A spring may bias the feature into the first configuration. The lock may include at least one of a button or a bar. A shaft may extend radially inward, relative to a housing of the handle, from the at least one of the button or the bar to the feature. At least a portion of the actuator and the feature may extend away from the shaft in the same direction. The feature may be substantially parallel to at least a portion of the actuator. The shaft may extend radially through an opening in the actuator. The lock may include the bar. The bar may extend laterally through an opening in the actuator. The plurality of teeth may face radially inward relative to a housing of the handle. The plurality of the teeth may face laterally outward relative to a housing of the handle. The rack may be curved. The rack may be recessed within a surface of the handle. The lock may be movable in a radial direction relative to a housing of the handle. A shape of the teeth may complement a shape of the feature. Additionally or alternatively, the shaft of the handle may translate along a track of the actuator.

In another example, a handle of a medical device may comprise: a rotatable actuator; a lock radially movable relative to the actuator and configured to radially move a feature relative to the actuator; and a rack having plurality of teeth separated from one another by a plurality of gaps. The lock may be configured to move the feature radially inward toward a handle housing from (a) a first configuration, in which the feature is disposed in a gap of the plurality of gaps, between two of the plurality of teeth, such that the two teeth inhibit the lever from rotating, to (b) a second configuration, in which the feature is disposed radially inward of the teeth, such that the actuator is rotatable.

Any of the handles described herein may have the following features. The feature may be biased into the first configuration.

In another example, a method of operating a medical device may comprise: with an actuator in a first position, depressing a lock radially inward relative to the actuator, thereby moving a feature radially inward of teeth of a stationary rack gear; while depressing the lock, rotating the actuator to a second position; and with the actuator in the second position, releasing the lock, thereby moving the feature so that the teeth inhibit movement of the feature in a direction of movement of the actuator.

Any of the methods or devices disclosed herein may have any of the following features. The method may further comprise: with the actuator in the second position, depressing the lock radially inward relative to the actuator, thereby moving the feature radially inward of the teeth of the stationary rack gear; while depressing the lock, rotating the actuator to a third position; and with the actuator in the third position, releasing the lock, thereby moving the feature so that the teeth inhibit movement of the feature in a direction of movement of the actuator. The lock may include a bar or a button.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "distal" refers to a direction away from an operator, and the term "proximal" refers to a direction toward an operator. The term "exemplary" is used in the sense of "example," rather than "ideal." The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate aspects this disclosure and together with the description, serve to explain the principles of the disclosure.

DETAILED DESCRIPTION

It may be desirable to lock actuators or controllers of medical devices (for example, levers) of duodenoscopes in a desired position. For example, it may be desirable to retain a lever that controls an elevator in a desired position. Such locks may free an operator to make use of a finger that would otherwise be used to retain the lever in position. Furthermore, the lever may require a high amount of force from an operator to retain the lever in place without a locking/retaining mechanism. Locking/retaining mechanisms may help to avoid fatigue by the user. The examples disclosed herein use fixed gear structures to lock/retain an actuator (e.g., a lever) in a desired position. Although elevator levers are described herein, it will be appreciated that the disclosed levers may also be used for other types of controls (e.g., steering of a distal tip of the duodenoscope).

Figure 1A:
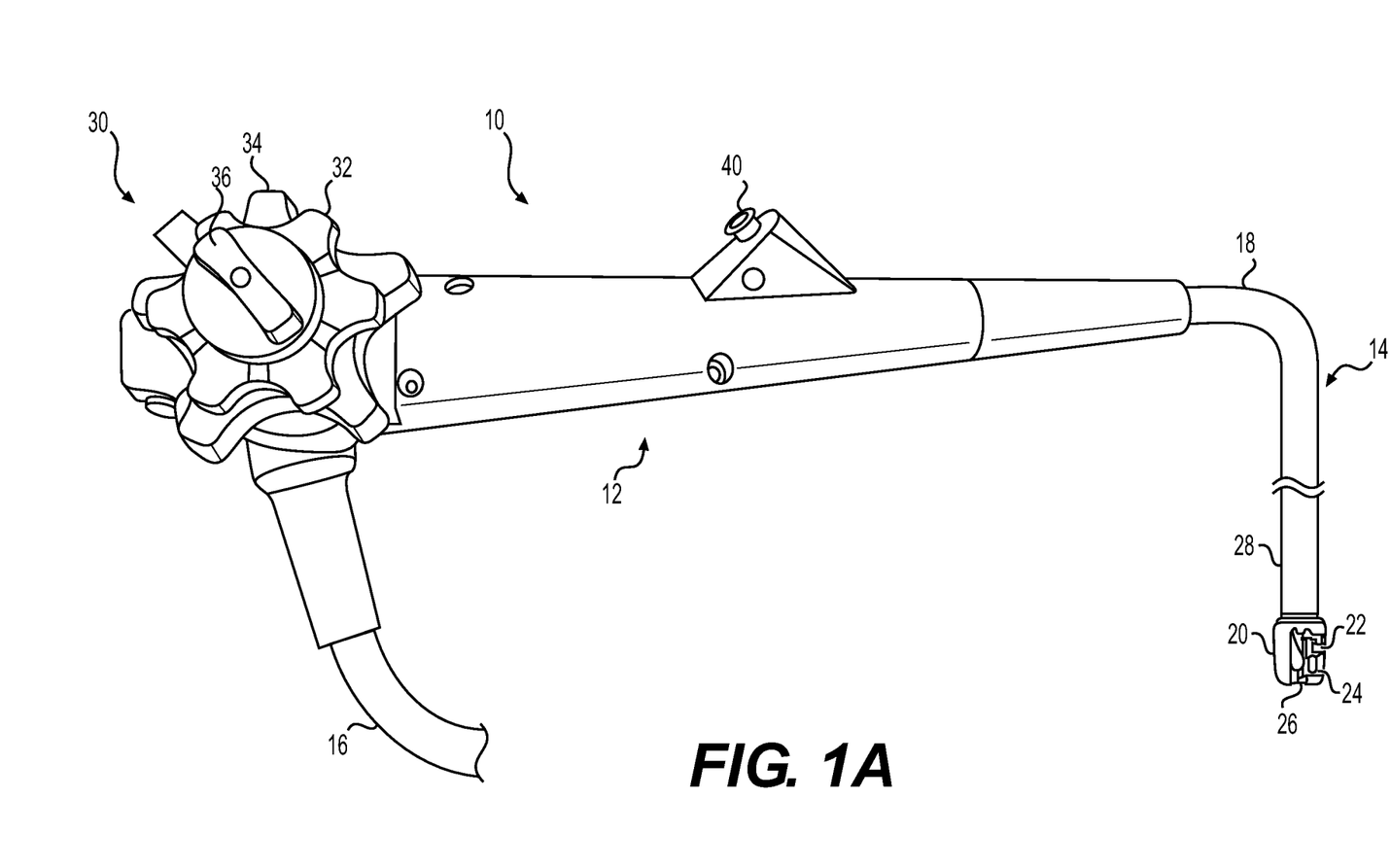
FIGS. 1A and 1B depict aspects of an exemplary duodenoscope.
Figure 1B:
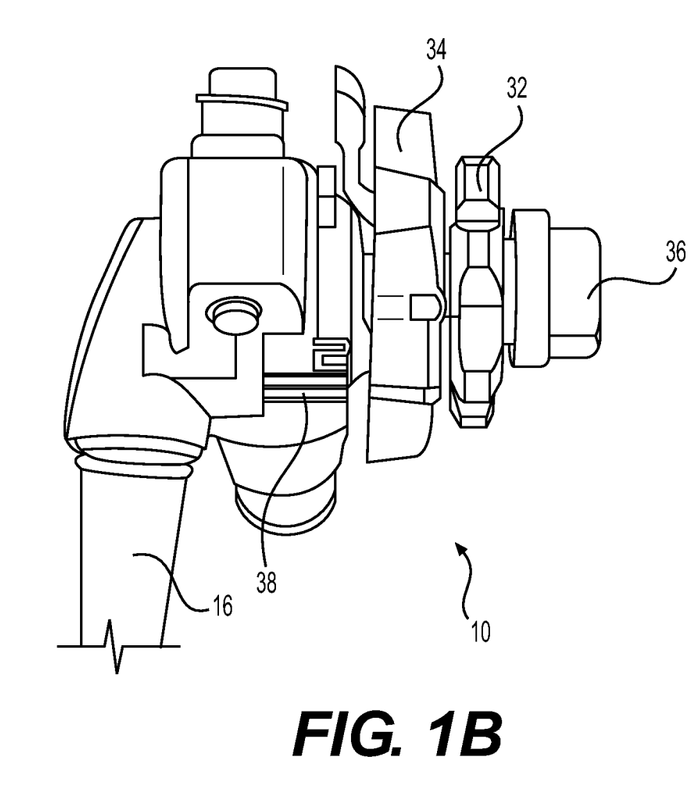

FIG. 1A depicts an exemplary duodenoscope 10 having a handle 12 and an insertion portion 14. FIG. 1B shows a proximal end of handle 12. Duodenoscope 10 may also include an umbilicus 16 for purposes of connecting duodenoscope 10 to sources of, for example, air, water, suction, power, etc., as well as to image processing and/or viewing equipment. Although the term duodenoscope may be used herein, it will be appreciated that other devices, including, but not limited to, endoscopes, colonoscopes, ureteroscopes, bronchoscopes, laparoscopes, sheaths, catheters, or any other suitable delivery device or medical device that may include an elevator or another actuatable distal tip component, may be used in connection with the devices and manufacturing methods of this disclosure. Although side-facing devices are particularly discussed, the embodiments described herein may also be used with front-facing endoscopes (e.g., endoscopes where a viewing element faces longitudinally forward) or any other device where a user may desire the ability to lock or unlock a portion of the device.

Insertion portion 14 may include a sheath or shaft 18 and a distal tip 20. Distal tip 20 may include an imaging device 22 (e.g., a camera) and a lighting source 24 (e.g., an LED or an optical fiber). Distal tip 20 may be side-facing. That is, imaging device 22 and lighting source 24 may face radially outward, perpendicularly, approximately perpendicularly, or otherwise transverse to a longitudinal axis of shaft 18 and distal tip 20.

Distal tip 20 may also include an elevator 26 for changing an orientation of a tool inserted in a working channel of duodenoscope 10. Elevator 26 may alternatively be referred to as a swing stand, pivot stand, raising base, or any suitable other term. Elevator 26 may be pivotable via, e.g., an actuation wire or another control element that extends from handle 12, through shaft 14, to elevator 26.

A distal portion of shaft 18 that is connected to distal tip 20 may have a steerable section 28. Steerable section 28 may be, for example, an articulation joint. Shaft 18 and steerable section 28 may include a variety of structures which are known or may become known in the art.

Handle 12 may have one or more actuators/control mechanisms 30. Control mechanisms 30 may provide control over steerable section 28 or may allow for provision of air, water, suction, etc. For example, handle 12 may include control knobs 32, 34 for left, right, up, and/or down control of steerable section 28. For example, one of knobs 32, 34 may provide left/right control of steerable section 28, and the other of knobs 32, 34 may provide up/down control of steerable section 28. Handle 12 may further include one or more locking mechanisms 36 (e.g., knobs or levers) for preventing steering of steerable section 28 in at least one of an up, down, left, or right direction. Handle 12 may include an elevator control lever 38 (see FIG. 1B). Elevator control lever 38 may raise and/or lower elevator 26, via connection between lever 38 and an actuating wire that extends from lever 38, through shaft 18, to elevator 26. A port 40 may allow passage of a tool through port 40, into a working channel of the duodenoscope 10, through sheath 18, to distal tip 20.

In use, an operator may insert at least a portion of shaft 18 into a body lumen of a subject. Distal tip 20 may be navigated to a procedure site in the body lumen. The operator may insert a tool (not shown) into port 40, and pass the tool through shaft 18 via a working channel to distal tip 20. The tool may exit the working channel at distal tip 20. The user may use elevator control lever 38 to raise elevator 26 and angle the tool toward a desired location (e.g., a papilla of the pancreatico-biliary tract). The user may use the tool to perform a medical procedure.

Figure 2A:
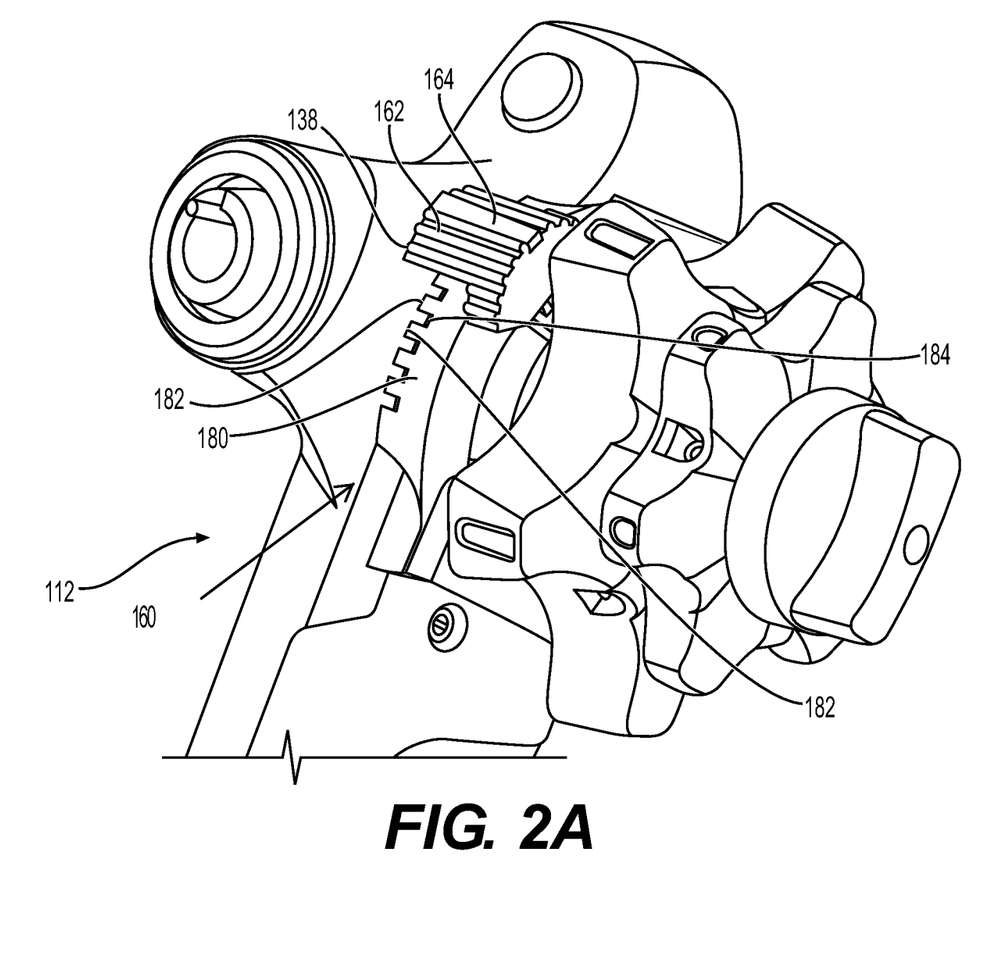
FIGS. 2A and 2B depict a first lever for use with the duodenoscope of FIGS. 1A-1B.
Figure 2B:
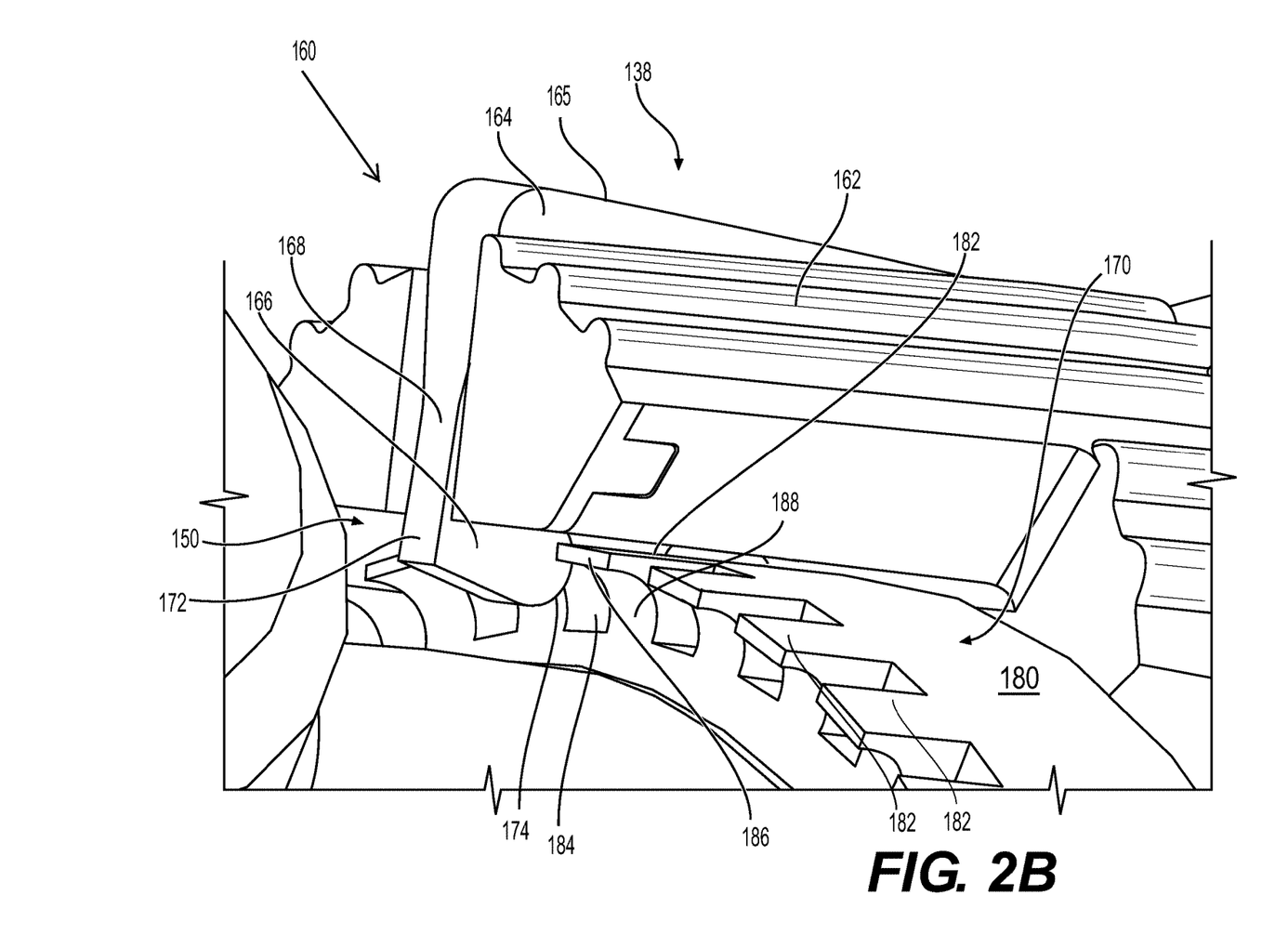

FIGS. 2A and 2B disclose views of a handle 112, which may have any of the properties of handle 12 of FIGS. 1A-1B. Handle 112 may have a locking/retaining mechanism 160. Handle 112 may have an elevator control lever 138, having any of the properties of elevator control lever 38 of FIG. 1B. Locking mechanism 160 includes a stationary rack gear 180 and features of elevator control lever 138 that interact with rack gear 180 in order to retain/lock elevator control lever 138 in a desired position.

Elevator control lever 138 may include a lever body 162 and a cross bar 164. Cross bar 164 may be an actuator for locking/retaining and/or releasing elevator control lever 138, in a desired position. A radially outer surface 165 of cross bar 164 may extend radially outwardly from lever body 162. Radially outer surface 165 of cross bar 164 may extend radially outwardly from lever body 162 by only a small amount in order to facilitate a user contacting lever body 162 and cross bar 164 without any uncomfortable protrusions. Cross-bar 164 may extend laterally (e.g., substantially perpendicularly to a longitudinal axis of handle 112) through at least a portion of elevator control lever 138. Elevator control lever 138 may have an opening (e.g., a slit) extending at least partially therethrough for receiving cross bar 164.

As shown in FIG. 2B, cross bar 164 may include an arm/shaft 168 that extends radially inward from radially outer surface 165. A feature, such as a tooth 166, may be disposed at a radially inward end of arm 168. Tooth 166 and lever body 162 may extend in substantially the same direction away from arm 168. A radially outward portion of cross bar 164 (having surface 165), arm 168, and tooth 166 may form a substantially C-shape. Tooth 166 may extend laterally inward (in a direction toward a center of handle 112). Tooth 166 may have a first end 172 and a second end 174. First end 172 may be flat, and second end 174 may be curved. Alternative shapes may be used for first end 172 and second end 174 within the scope of the disclosure. A radially outer surface 165 of cross bar 164 (and other portions of cross bar 164) may extend further in the lateral direction than tooth 166 does, in order to facilitate tooth 166 engaging with stationary rack 180, as discussed in further detail below. Cross-bar 164 (including arm 168 and tooth 166) may be substantially flat (i.e., side surfaces of cross-bar 164 may be planar).

Elevator control lever 138 and cross bar 164 may include any suitable material. For example, elevator control lever 138 and/or cross bar 164 may include polymers (e.g., plastic), composites, or metal. In one example, elevator control lever 138 may be formed from plastic, and cross bar 164 may be formed from metal. Elevator control lever 138 may be formed of a single, unitary material or a plurality of components secured to one another. Cross-bar 164 may be formed of a single, unitary material or a plurality of components secured to one another.

Stationary rack gear 180 may include a plurality of teeth 182, separated from one another by gaps 184. Rack gear 180 may have a curved shape, to match an arcuate path traveled by elevator control lever 138 when lever 138 is actuated. Teeth 182 may extend in a laterally outward direction (away from a center of handle 112). As shown in FIG. 2B, each tooth 182 may have a ledge 186 that extends further in a lateral direction than a remainder of tooth 184. A body 188 of tooth 182 may be recessed from ledge 186 and may have a rounded/arcuate radially inner surface. A shape of teeth 182 and gaps 184 may complement a shape of tooth 166. For example, rounded/arcuate radially inner surface of body 188 may complement a rounded shape of tooth 166.

Stationary rack gear 180 may be formed integrally with a housing of handle 112. Alternatively, stationary rack gear 180 may be a separate piece that is fixedly attached to a housing of handle 112. Stationary rack gear 180 may be one single piece or may be formed from a plurality of pieces. Stationary rack gear 180 may be formed from any suitable material or combination of materials (including, e.g., polymer, such as plastic, composite, or metal).

In operation, a user may make contact with lever body 162 of elevator control lever 138 in order to raise or lower the elevator. In doing so, the user may depress cross bar 164 in a radially inward direction, by exerting a radially inward force on radially outward surface 165 of cross bar 164. Cross-bar 164 may be rigid such that tooth 166 moves radially inward. As cross bar 164 is depressed, a radially outward surface of tooth 166 of cross bar 164 may move radially inward of ledge 186, such that tooth 166 does not interfere with teeth 182 of gear rack 180. Thus, when cross bar 164 is depressed, the user may move elevator control lever 138 to raise or lower the elevator.

Cross-bar 164 may be biased in a radially outward direction to the configuration of FIG. 2B. For example, cross bar 164 may have shape memory properties, or a spring may exert a radially outward force on cross bar 164. Alternatively, cross bar 164 may attach to lever 138 via a living hinge or other biased hinge, so that a normal (i.e., relaxed) position of cross bar 164 is as shown in FIG. 2B. Cross-bar 164 therefore moves relative to lever 138. Therefore, when the user releases contact from surface 165 of cross bar 164, cross bar 164 may move radially outward to the configuration of FIG. 2B. In the configuration of FIG. 2B, tooth 166 may be positioned within gap 184 such that tooth 166 interferes with teeth 182 of stationary gear rack 180 (e.g., tooth 166 may be between two adjacent 186) along a direction of movement of lever 138. In the configuration of FIG. 2B, a position of tooth 166 of cross bar 164 may prevent elevator control lever 138 from being moved to raise or lower the elevator. Interaction between cross bar 164 and stationary rack gear 180 may thus retain elevator control lever 138 in a desired position (e.g., locking elevator control lever 138).

Because stationary rack gear 180 may have a plurality of teeth 182 and gaps 184, locking mechanism 160 may serve to retain elevator control lever 138 within a plurality of positions, and therefore retain elevator 26 in any of a number of positions. A user may choose a position at which to lock elevator control 138. The user may also depress cross bar 164 to move elevator control lever 138 and then release cross bar 164 to retain/lock elevator control lever 138 in a new position.

Figure 3A:
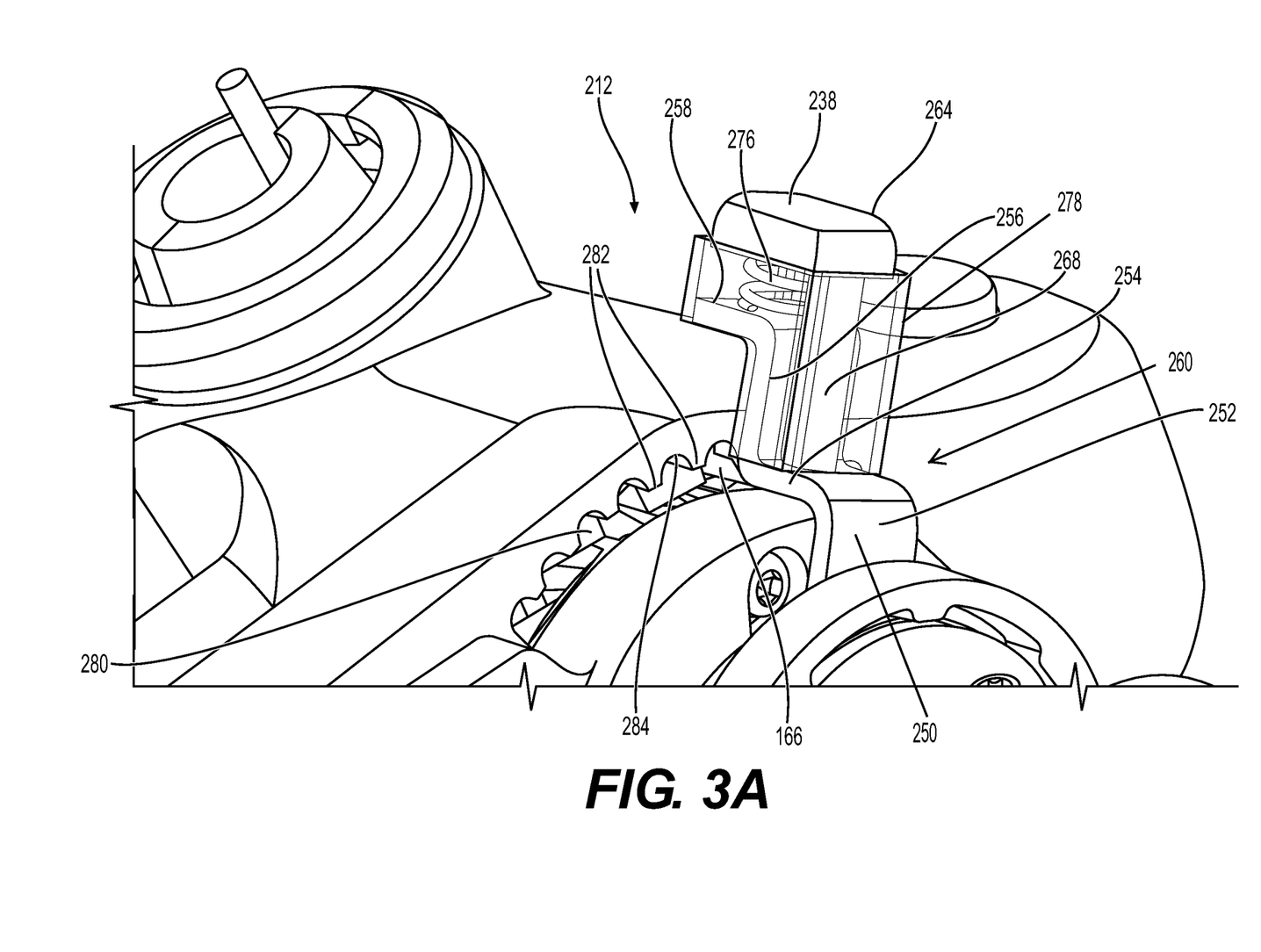
FIGS. 3A and 3B depict a second lever for use with the duodenoscope of FIGS. 1A-1B.
Figure 3B:
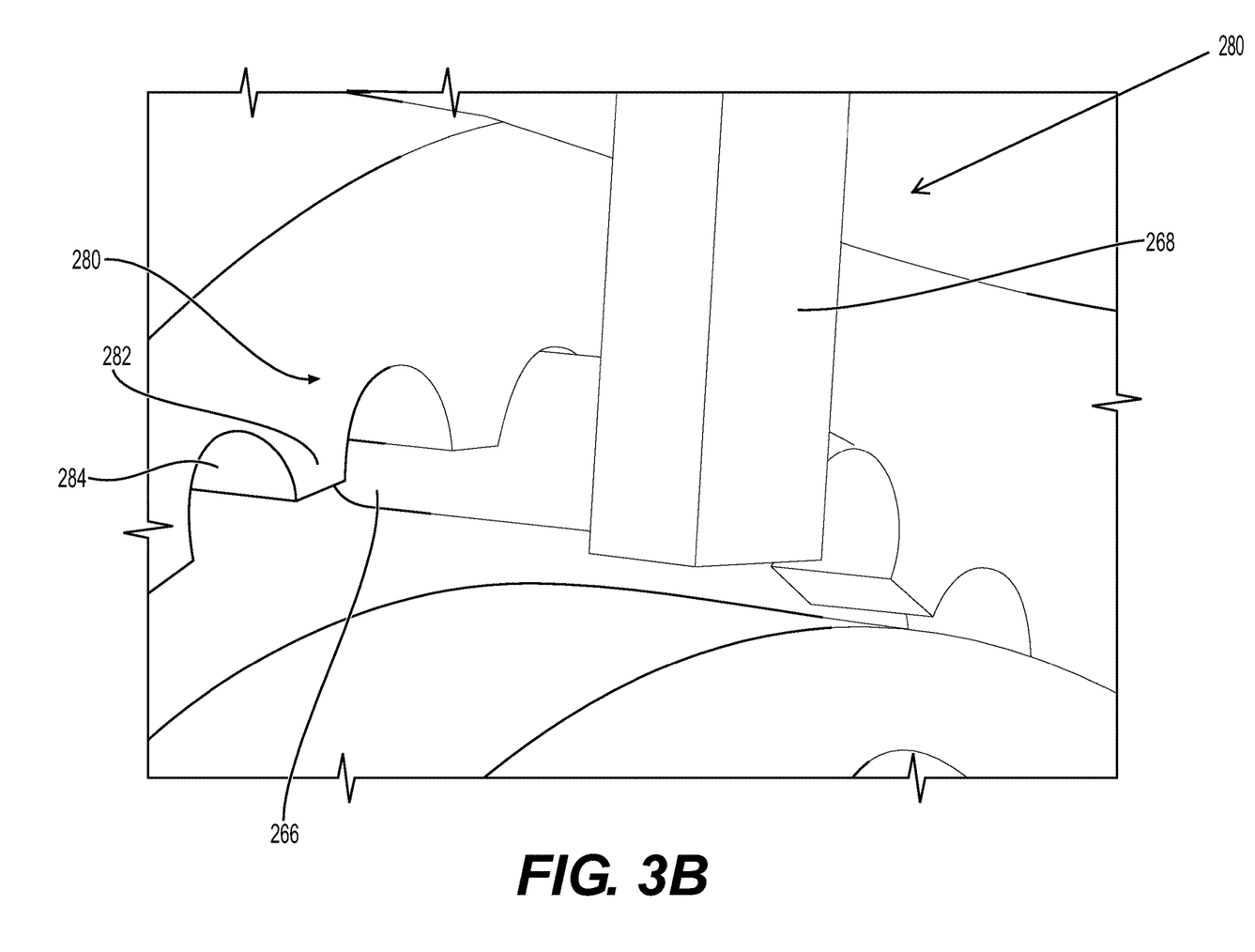

FIGS. 3A and 3B depict an alternative handle 212, which may have any of the properties of handles 12 or 112, except as specified below. Some of the structures of FIG. 3A are transparent on FIG. 3B, in order to show details of particular aspects. Where feasible, parallel reference numbers are used to denote like structures between handles 212 and 112. Handle 212 may include a locking mechanism 260. Locking mechanism 260 may include an elevator control lever 238 that interacts with a stationary rack gear 280.

Elevator control lever 238 may have a lever body 250 (shown in FIG. 3A but omitted from FIG. 3B for clarity). Lever body 250 may have an angled shape that conforms to a surface of handle 212. As shown in FIG. 3A, lever body 250 may have two segments 252, 256 that extend along a substantially radial direction. Between segments 252 and 256 is a segment 254 that extends substantially laterally, perpendicular to segments 252 and 256. A radially outer end of segment 256 may be joined to a segment 258 that extends substantially parallel to segment 254. Segment 254 may form an end of lever body 250. Lever body 250 may be one single piece or may be formed from a plurality of pieces. Lever body 250 may be formed from any suitable material or combination of materials (including, e.g., polymer, such as plastic, composite, or metal).

A button 264 may extend approximately parallel to segment 258 and may be disposed radially outward of segment 258. Button 264 may be an actuator for locking/retaining lever 238 in a desired position and/or releasing/unlocking lever 238. A spring 276 may extend between segment 258 of lever body 250 and button 264. Button 264 may be movable in a substantially radial direction, approximately parallel to segments 252 and 256. Spring 276 may bias button 264 in a substantially radially outward direction (which, as discussed below, may be a locked configuration). Other, alternative means may also be used to bias button 264 radially outward, into a configuration in which button 264 is not depressed. For example, button 264 may have shape memory properties.

A shaft 268 may be fixed to and extend radially inward from button 264 (e.g., from an end of button 264). Shaft 268 may extend substantially parallel to segments 252 and 256. Segment 256 may be disposed between shaft 268 and a housing of handle 212. Shaft 268 may extend radially inward through an opening in segment 254 and may be movable relative to lever body 250, along with button 238. Button 238 and shaft 268 may be one single piece or may be formed from a plurality of pieces. Button 238 and shaft 268 may be formed from any suitable material or combination of materials (including, e.g., polymer, such as plastic, composite, or metal).

Housing 278 may enclose one or more of segment 256, segment 258, spring 276, and/or portions of shaft 268 that are radially outward of segment 254. Button 264 and shaft 268 may be movable relative to housing 278.

As shown in FIG. 3B, a feature, such as a peg 266, may extend laterally inward from shaft 268, substantially parallel to segments 254 and 258. Peg 266 may extend in a direction toward an interior of handle 212 (toward segment 256). Peg 266, segment 254, and button 264 may extend away from shaft 268 in substantially the same direction. Peg 266, shaft 268, and button 264 may form approximately a C-shape. Peg 266 may have, for example, a rounded shape or any other suitable shape. Peg 266 and shaft 268 may be one single piece or may be formed from a plurality of pieces. Peg 266 and shaft 268 may be formed from any suitable material or combination of materials (including, e.g., polymer, such as plastic, composite, or metal).

Stationary rack gear 280 may be formed on a surface of a housing of handle 212 that faces radially inward. For example, stationary rack gear 280 may be a cut-out formed in a housing of handle 212. A plurality of teeth 282 and a plurality of gaps 284 between teeth 282 may be formed on the radially-inward facing surface of the housing of handle 212. Teeth 282 may face/extend radially inward. Because stationary rack gear 280 is formed on a cutout, teeth 282 may not interfere with a finger/hand of a user (which may cause an operator's glove to rip, for example). Stationary rack gear 280 may have a curved shape to correspond to a path of motion of lever 238.

Gaps 284 may have a curved (e.g., substantially semicircular) cross-sectional shape. Alternatively, gaps 284 may have another shape. A shape of gaps 284 may complement a shape of peg 266.

Stationary rack 280 may be integrally formed with a housing of handle 212 or may be a separate piece from the housing of handle 212. Stationary rack 280 may be one single piece or may be formed from a plurality of pieces. Stationary rack 280 may be formed from any suitable material or combination of materials (including, e.g., polymer, such as plastic, composite, or metal).

In operation, a user may depress button 264, which may move shaft 268 in a substantially radially inward direction, thereby moving peg 266 in a substantially radially inward direction. Peg 266, when moved in a substantially radially inward direction, may clear teeth 282 of stationary gear rack 280, such that teeth 282 do not interfere with peg 266. In other words, an entirety of peg 266 may be disposed radially inward of teeth 282. Thus, when button 264 is depressed, elevator control lever 238 (including lever body 250) may be moved to adjust a positioning of the elevator.

When the user releases button 264, spring 276 may exert a force on button 264 in a substantially radially outward direction (i.e., button 264 may be biased to the undepressed configuration). As button 264 moves radially outward, shaft 268 and peg 266 also move radially outward. When button 264 is not depressed, peg 266 may be disposed within a gap 284 of stationary rack gear 280. At least a portion of peg 266 may be disposed radially inward of a radially outward edge of surrounding teeth 282. Teeth 282 may interfere with peg 266 along a direction of movement of lever 238. Teeth 282 may thus limit movement of peg 266 and, thus, elevator control lever 238.

Because stationary rack gear 280 may have a plurality of teeth 282 and gaps 284, locking mechanism 260 may serve to retain elevator control lever 238 at a plurality of positions, and thereby secure elevator 26 at any of a plurality of positions. A user may choose a position at which to lock elevator control 238. The user may also depress button 264 to move elevator control lever 238 and then release button 264 to retain/lock elevator control lever 238 in a new position.

FIGS. 4A-4D depict an alternative handle 312, which may have any of the properties of handles 12, 112, or 212 except as specified below. Where feasible, parallel reference numbers are used to denote like structures between handles 312, 212, and 112. Similar to handle 212 depicted in FIGS. 3A and 3B, handle 312 may include a locking mechanism 360. Locking mechanism 360 may include an elevator control lever 338 that interacts with a stationary rack gear 380, shown in FIGS. 4B and 4C and to be described further herein.

Figure 4A:
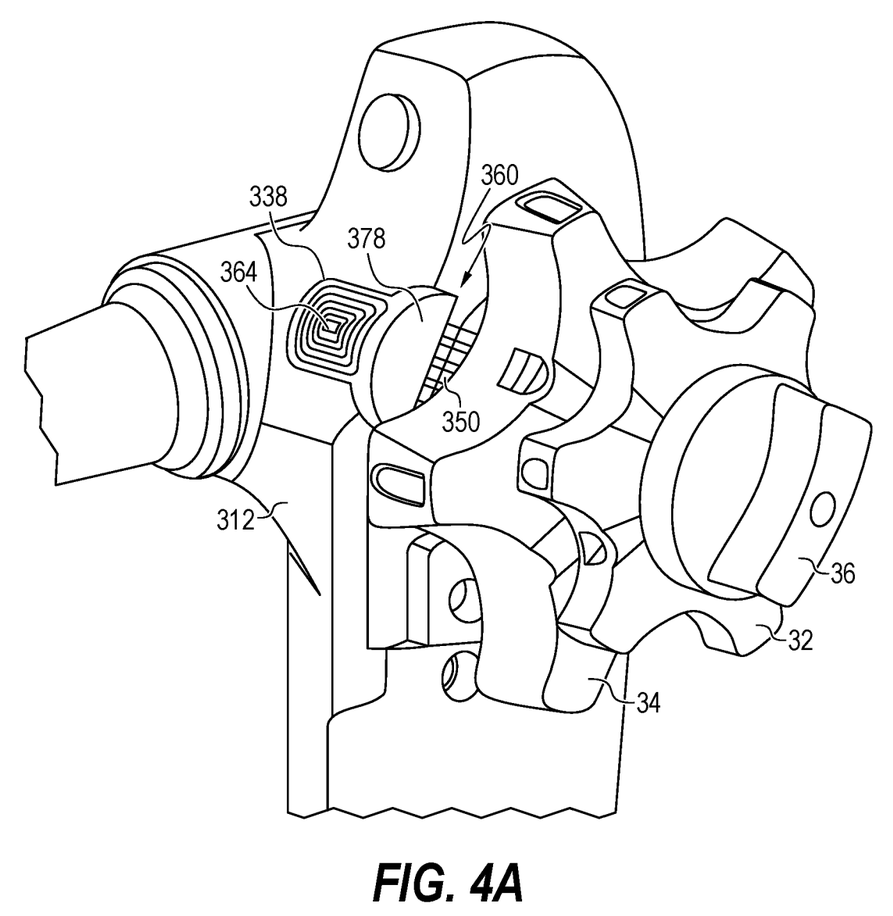
FIGS. 4A, 4B, 4C, and 4D depict a third lever for use with the duodenoscope of FIGS. 1A-1B.

Elevator control lever 338 may include a button 364 positioned radially outward from adjacent portions of handle 312, toward a user. Button 364 may be an actuator for locking/retaining elevator control lever 338 in a desired position and/or releasing/unlocking lever 338. An outermost surface of button 364 may include a smooth surface, a rough surface (i.e. textured), or otherwise be padded to provide comfort to the user and/or to facilitate a more secure grip. The elevator control lever 338, including its button 364, like any other structure of locking mechanism 360, may be comprised of a variety of materials, such as composites, stainless steel, plastics, polymers, or any alternative or combination of materials commonly used in the art. For example, button 364 may be comprised of a composite material, and a remainder of control lever 338 may be comprised of a stainless steel or plastic.

Figure 4B:
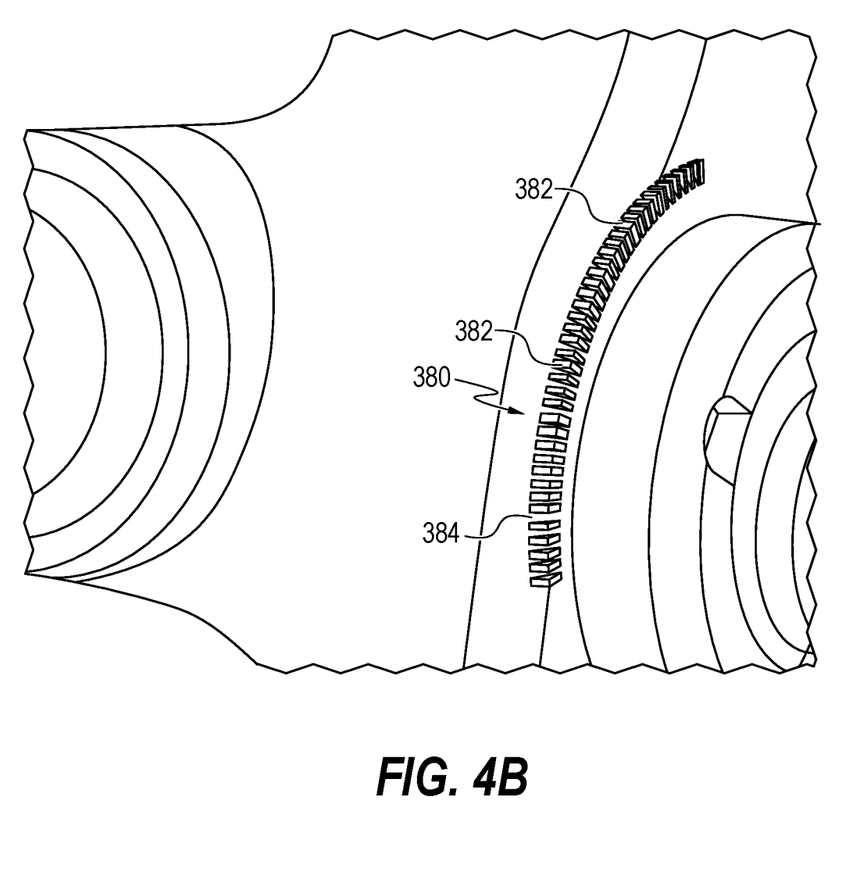

Button 364 is surrounded by, and translates within, a housing 339. Housing 339 is ring-like and defines an internal aperture 339' that receives and houses button 364. FIG. 4D shows housing 339 and aperture 339', without button 364. iButton 364, when pressed, will translate relative to housing 339 towards surfaces of handle 312.

Figure 4C:
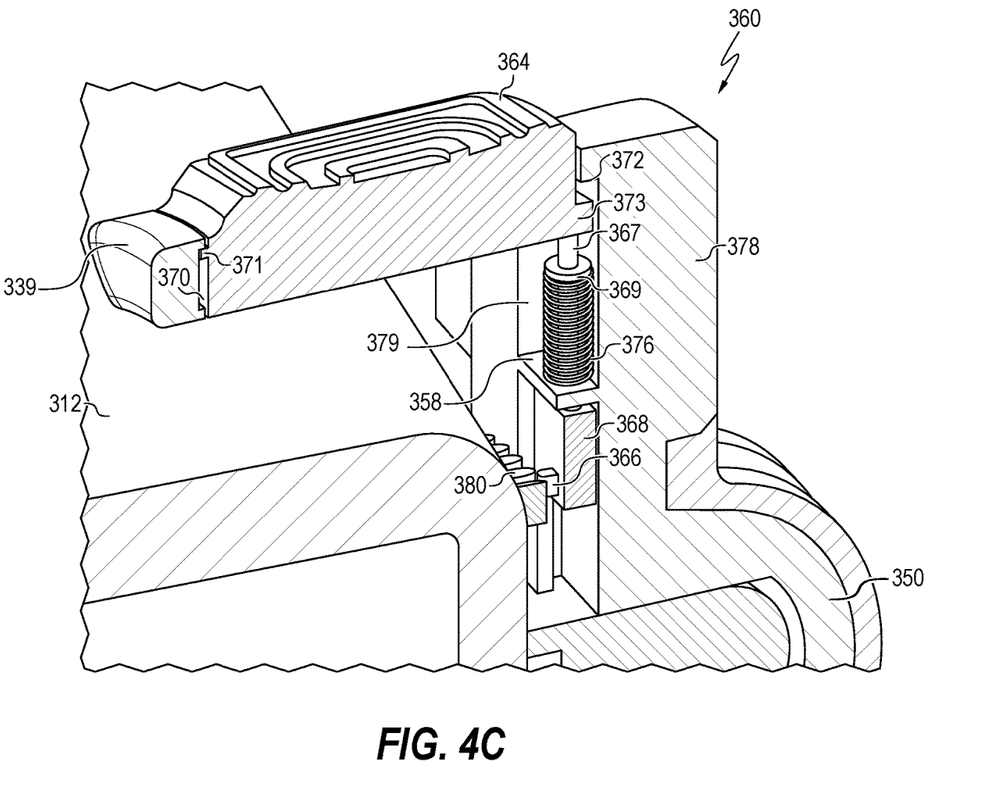
Figure 4D:
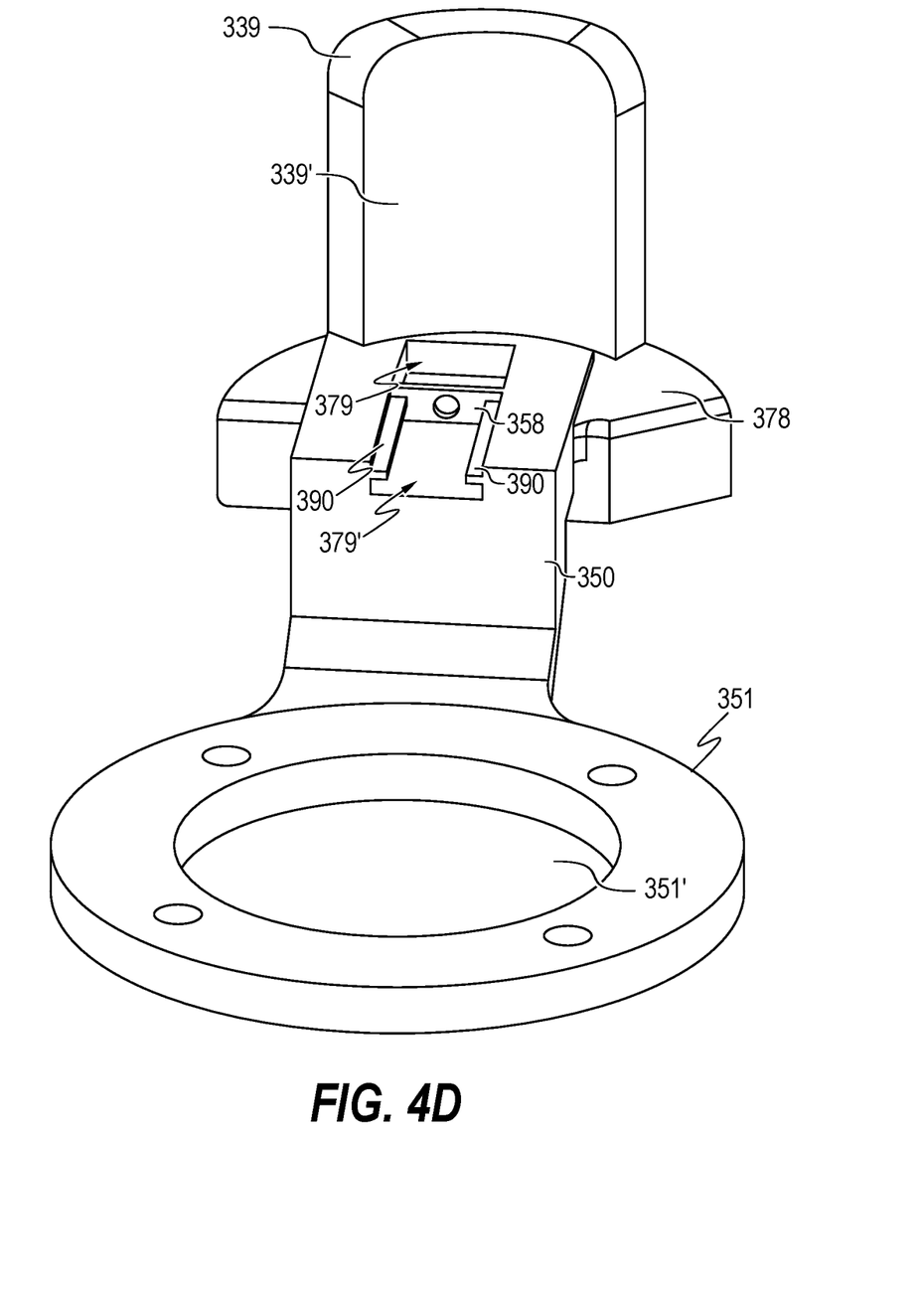

Housing 339 is integral with, or otherwise connected to, and fixed to an arm 378 (shown in more detail in FIGS. 4C and 4D). Arm 378 has a semi-circular cross-sectional shape (see FIG. 4A) and provides support to control lever 338 and raises control lever 338 away from outer surfaces of handle 312, to limit undesired interactions during use between the control lever 338 and the handle 312 or other components of device 10 of FIG. 1. Arm 378 is integral with, or otherwise connected to, and fixed to a lever body 350. Alternatively, arm 378 may be a separate component coupled to lever body 350 by means of glue, fasteners, a press-fit, or any other means commonly known in the art. Lever body 350 may have a shape that conforms to, complements, or otherwise wraps around, a surface of handle 312.

Lever body 350 is integral with, or otherwise connected to, and fixed to a ring 351 that movably couples control lever 338 to the remainder of handle 312. Ring 351 encloses and defines an inner aperture 351' that receives structure for connecting knobs 32, 34 to parts internal to the handle housing, for causing articulation of the distal end of the scope. Ring 351 mounts to the handle housing in a manner that permits rotation of ring 351 about its central axis, as locking lever 338 is rotated/pivoted by a user.

FIG. 4B shows an outer surface of handle 312. Stationary rack 380 may be integrated into or otherwise formed with handle 312. Stationary rack 380 may comprise a plurality of teeth 382 separated by a plurality of gaps 384. Stationary rack 380 may be curved along the handle 312 so as to engage with the elevator control lever 338 along the entire length of the path of motion of lever 338. Stationary rack 380 may have a radius of curvature that is the same as or approximately the same as the radius of curvature of the path of motion of lever 338. The plurality of teeth 382 and the plurality of gaps 384 may be one size or a variety of sizes so as to engage with lever 338. Each of the plurality of teeth 382 may extend perpendicularly away from the outer surface of handle 312. Stationary rack 380 may be an integral component of handle 312 or a separate component fixedly coupled to handle 312 by means of glue, a press-fit, ultrasonic welding, fasteners, or any other means commonly known in the art. In such a configuration, stationary rack 380 may be comprised of the same material as handle 312 or a different material. For example, handle 312 may be comprised of a polycarbonate material, and stationary rack 380 may be comprised of a stainless steel.

FIG. 4C shows a cross-section of locking mechanism 360 to demonstrate the interaction between internal components of control lever 338 and stationary rack 380. A protrusion 371 of button 364 travels within a recess 370 of housing 339 and prevents the button 364 from travelling too far, acting as a stop to limit radially inward movement of button 364. For example, in a pressed configuration of button 364, protrusion 371 travels downward within recess 370 of housing 339. Button 364 is stopped (i.e. can no longer be pressed) when a bottom face of protrusion 371 abuts a bottom face within the recess 370. Similarly, button 364 is prevented from continuous upward travel once a top face of protrusion 371 abuts a top face of recess 370, or, as described below, a distal shaft 368 abuts segment 358, as described below. The length and depth of recess 370 may vary according to the desired amount of travel for button 364. On the opposite side of button 364, a protrusion 373 of button 364 travels within an opening 379 of arm 378 and lever body 350. A top face of protrusion 373 may abut a bottom face of 372 of opening 379 in a first configuration, as shown in FIG. 4C. Opening 379 of arm 378 and lever body 350 contains a shaft 367. Opening 379 may function to provide space for the working assembly and to provide linear space for distal shaft 368, protrusion 373, and shaft 367 to move. Opening 379 may be defined by alternative features, such as lever body 350 or alternative configurations of arm 378. Shaft 367 may be fixed to and extend radially inward from button 364 (e.g. from an end or bottom surface of button 364). Shaft 367 may extend substantially parallel relative to arm 378 and/or extend perpendicularly to the bottom surface of button 364. Shaft 367 may further comprise a flange/extension 369. Extension 369 may extend radially outwardly or perpendicularly from a center axis of shaft 367. Extension 369 may be utilized to hold or confine a spring 376 to a lower portion (as shown) or upper portion of shaft 367. However, extension 369 may be omitted in other embodiments such that the spring 376 is not confined to a limited portion of the shaft 367. Shaft 367 may extend radially inward through an opening in a wall/segment 358 and may be movable relative to lever body 350 and arm 378, along with button 364. Segment 358 may extend perpendicularly outward from a surface defining opening 379, and divides opening 379 into a portion above segment 358 (housing spring 376) and a portion below segment 358. Button 364 and shaft 367 may be one single piece or may be formed from a plurality of pieces. Shaft 367 may be circular in cross-section (as shown), square, rectangular, or otherwise shaped to fit within opening 379 and the opening in segment 358.

A distal end of shaft 367 may include a distal shaft 368. Distal shaft 368 may be a separate component of shaft 367 or be otherwise formed with a remainder of shaft 367 (i.e. as one component). Distal shafts 368 is confined below segment 358 to, along with other portions of shaft 367 and spring 369, control the displacement of button 364. Segment 358 may extend the entire width of opening 379 to create two openings (379 and 379'), as shown in FIG. 4D. Alternatively, segment 358 may extend a partial width of opening 379 such that opening 379 is continuous above and below segment 358. Distal shaft 368 may be rectangular in cross-section, as shown, or otherwise shaped to fit within opening 379'. Distal shaft 368 may include grooves in its sides that travel along a track 390 (shown in FIG. 4D) extending within opening 379, 379'. Track 390 can be utilized to ensure distal shaft 368 remains in position to prevent jamming or breakage of the locking mechanism 360.

As shown in FIG. 4C, a feature, such as a peg 366, may extend laterally outward from distal shaft 368 and toward an interior of handle 312. Peg 366, distal shaft 368, shaft 367, and button 364 may form approximately a C-shape. Peg 366 may have, for example, a rounded shape or any other suitable shape to fit between teeth 382 and within gaps 384 of the rack gear 380. Gaps 384 and teeth 382 may be shaped similarly to the gaps and teeth of previous embodiments, described above with reference to FIGS. 2A-3B.

The embodiment of FIGS. 4A-4D operates in a similar manner to the embodiment described in FIGS. 2A-3B. For example, in a first configuration, when button 364 is released, button 364 is biased upward by spring 376. In this released state, a top surface of shaft 368 may touch or abut a bottom surface of segment 358 and prevent additional lateral, or upward, movement of the button 364. Additionally or alternatively, protrusion 371 may touch or abut a bottom surface of opening 370 in the released state. This may occur simultaneously as the top surface of shaft 368 touches or abuts the bottom surface of segment 358 or this may occur as a fail-safe, for example, if protrusion 358 fails during use. Additionally, in this configuration, peg 366 is positioned within a gap 384 and between teeth 382. Accordingly, in this position, the control lever 338 is locked, unmovable, and cannot pivot or rotate.

To unlock the lever 338, a user may depress button 364. When button 364 is depressed, the spring 376 is depressed and shaft 367 and distal shaft 368 are lowered within openings 379, 379'. In effect, peg 366 is moved in a substantially radially inward direction, clearing the bottom of teeth 382. With peg 366 below teeth 382, elevator control lever 338 is movable (i.e. in an unlocked position) and can be pivoted/rotated. In alternating between the first configuration and the second configuration, a user can achieve a desired position of the elevator or accessory tool (not shown).

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Additionally, a variety of elements from each of the presented embodiments can be combined to achieve a same or similar result as one or more of the disclosed embodiments. For example, elements of FIGS. 2A-2B may be combined with one or more elements of the embodiments depicted in FIGS. 3A-3B and/or 4A-4D. Accordingly, the invention is not to be considered as limited by the foregoing description.

We claim:

1. A handle of a medical device, the handle comprising:
   a handle housing having a stationary rack gear including a plurality of teeth separated from one another by a plurality of gaps; and
   a locking mechanism having a plurality of segments, a button, a shaft, and a peg, wherein the locking mechanism is configured to lock an elevator of the medical device in a position in a first configuration, and wherein the locking mechanism is configured to permit movement of the elevator of the medical device in a second configuration, wherein the plurality of segments includes:
a first segment;
a second segment joined to the first segment, wherein the second segment is substantially perpendicular to the first segment; and
a third segment joined to the second segment, wherein the third segment is substantially parallel to the first segment;
wherein the shaft extends substantially parallel to and externally of the second segment, wherein the shaft extends through an opening of the third segment, and wherein the peg extends from the shaft;
wherein the locking mechanism is configured to move the peg radially relative to the stationary rack gear from (a) a first configuration, in which the peg is disposed in a first gap of the plurality of gaps, the first gap being between two teeth of the plurality of teeth, such that the two teeth inhibit the locking mechanism from rotating; to (b) a second configuration, in which the peg is disposed entirely radially inward of the two teeth of the plurality of teeth, such that the locking mechanism is rotatable relative to the stationary rack gear, wherein, in the second configuration, the two teeth are disposed radially between the peg and the button.

2. The handle of claim 1, wherein the stationary rack gear is disposed on a radially-inward facing surface of the handle housing.

3. The handle of claim 2, wherein the plurality of teeth extend radially inward relative to the radially-inward facing surface of the handle housing.

4. The handle of claim 1, wherein a spring is disposed between the button and the first segment of the locking mechanism.

5. The handle of claim 4, wherein the spring is configured to bias the button in the first configuration, and wherein the first configuration is a locked configuration.

6. The handle of claim 4, wherein the shaft is adjacent to the spring and the second segment.

7. The handle of claim 1, wherein the second segment is perpendicular to the peg.

8. The handle of claim 1, further comprising a fourth segment, wherein the fourth segment is parallel to the second segment and perpendicular to the first segment and the third segment.

9. The handle of claim 8, wherein the first segment, the second segment, the third segment, and the fourth segment form an S-shape.

10. The handle of claim 1, wherein wherein the peg extends perpendicularly from the shaft.

11. The handle of claim 1 wherein the peg, the shaft, and the first segment form a C-shape.

12. The handle of claim 1, wherein the shaft is external to and non-intersecting with the first segment.

13. A handle of a medical device, the handle comprising:
a handle body having a stationary rack gear disposed thereon, wherein the stationary rack gear includes a plurality of teeth; and
a locking mechanism comprised of a button, a peg, a spring, and a body, wherein the body is comprised of a plurality of segments arranged to conform to an outer surface of the handle body,
wherein the plurality of segments includes:
a first segment extending along and adjacent to an outer surface of the handle body;
a second segment joined to the first segment;
a third segment joined to the second segment; and
a fourth segment joined to the third segment; and
wherein the first segment and the third segment are substantially perpendicular to the second segment and the fourth segment:
wherein the spring extends between the button and the first segment of the plurality of segments,
wherein the stationary rack gear is disposed between the peg and the button, and wherein the button is configured to move the peg radially relative to the stationary rack gear.

14. The handle of claim 13, wherein the locking mechanism further includes a shaft, wherein the shaft is fixed to the button, wherein the shaft extends through an opening of the third segment, wherein the peg extends perpendicularly from the shaft, and wherein the shaft is adjacent to the spring, the first segment, and the second segment.

15. The handle of claim 13, wherein the locking mechanism is configured to lock an elevator of the medical device in a position in a first configuration, and wherein the locking mechanism is configured to permit movement of the elevator of the medical device in a second configuration.

16. The handle of claim 13, wherein the plurality of teeth are disposed on a radially-inward facing surface of a cutout of the handle, and wherein each tooth of the plurality of teeth extend radially inward from the radially-inward facing surface of the handle.

17. The handle of claim 13, wherein no intervening structure exists between the first segment and the handle body.

18. A method of operating a medical device, the method comprising:
with an actuator of a handle of the medical device in a first position, depressing a button of a locking mechanism of the actuator radially inward, thereby moving a peg radially inward relative to (1) a body of the locking mechanism and (2) a plurality of teeth disposed on a radially-inward facing surface of a cutout formed in the handle, wherein each tooth of the plurality of teeth extend radially inward from the radially-inward facing surface of the handle;
while depressing the button, rotating the actuator to a second position; and
with the actuator in the second position, releasing the button, thereby moving the peg radially outward relative to (a) the body of the locking mechanism and (b) the plurality of teeth so that the plurality of teeth inhibit rotation of the peg,
wherein the body of the locking mechanism is comprised of:
a first segment;
a spring that extends between the first segment and the button;
a second segment joined to the first segment;
a third segment joined to the second segment; and
a fourth segment joined to the third segment; and
wherein the first segment and the third segment are (1) perpendicular to the second segment and the fourth segment and (2) parallel to the peg.

19. The method of claim 18, wherein the locking mechanism further includes a shaft, wherein the peg extends perpendicularly from the shaft, and wherein the shaft is moveable within an opening of the third segment.

20. The method of claim 19, wherein the shaft is adjacent to and external to the spring, the first segment, and the second segment.

* * * * *